(12) United States Patent
Dubois et al.

(10) Patent No.: US 7,732,639 B2
(45) Date of Patent: Jun. 8, 2010

(54) PROCESS FOR THE PREPARATION OF ACRYLIC ACID COMPRISING A PARTIAL OXIDATION OF PROPANE TO PROPYLENE

(75) Inventors: Jean-Luc Dubois, Millery (FR); Stephanie Serreau, Oullins (FR); Fabienne Desdevises, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 11/775,014

(22) Filed: Jul. 9, 2007

(65) Prior Publication Data

US 2008/0004468 A1 Jan. 3, 2008

Related U.S. Application Data

(63) Continuation of application No. PCT/FR2006/000111, filed on Jan. 18, 2006.

(30) Foreign Application Priority Data

Jan. 21, 2005 (FR) ................................ 05 00643

(51) Int. Cl.
*C07C 51/42* (2006.01)
(52) U.S. Cl. .................................................. 562/600
(58) Field of Classification Search ............. 562/600
See application file for complete search history.

(56) References Cited

U.S. PATENT DOCUMENTS

| 5,831,124 A * | 11/1998 | Machhammer et al. ...... 562/600 |
| 6,492,548 B1 | 12/2002 | Brockwell et al. |
| 7,332,625 B2 * | 2/2008 | Dubois et al. ............... 562/549 |
| 2003/0187298 A1 | 10/2003 | Borgmeier et al. |

FOREIGN PATENT DOCUMENTS

| BE | 896443 | 10/1983 |
| EP | 0 253 409 | 7/1987 |
| EP | 0 274 681 | 12/1987 |
| EP | 0253409 | 1/1988 |
| EP | 0 293 224 | 5/1988 |
| EP | 0274681 | 7/1988 |
| EP | 0293224 | 11/1988 |

* cited by examiner

*Primary Examiner*—Taylor Victor Oh
(74) *Attorney, Agent, or Firm*—Millen, White, Zelano & Branigan, P.C.

(57) ABSTRACT

The invention relates to a method for preparing acrylic acid by oxidizing propylene and then acrolein, involving the recycling of gases that had not reacted by means of a partial oxidation of the propane, in parallel, at the end of the acrylic acid recovery step, then returning, to the propylene-converting reactor, a gas rich in both propane and propylene having been subjected to a second passage in the acrylic acid recovery column.

4 Claims, 3 Drawing Sheets

PROCESS FOR THE PREPARATION OF ACRYLIC ACID COMPRISING A PARTIAL OXIDATION OF PROPANE TO PROPYLENE

CROSS-REFERENCE TO RELATED APPLICATIONS

This application is a continuation of International Application PCT/FR06/000111, filed Jan. 18, 2006, which claims priority to French Application No. 05/00643, filed Jan. 21, 2005, each of which is incorporated by reference in its entirety herein.

FIELD OF THE INVENTION

The present invention relates to the preparation of acrylic acid from propylene comprising recycling of gases with a propane-to-propylene oxidation stage.

BACKGROUND OF THE INVENTION

The production of acrylic acid generally consists of oxidation in 2 stages, on the one hand a first stage of oxidation of propylene to acrolein and on the other hand a second stage of oxidation of acrolein to acrylic acid.

However, productivity is limited by significant constraints, such as inflammability and the dangers of explosion of the propylene/air/nitrogen/steam mixture, removal of the quantity of heat produced from the reactor, as well as the sensitivity of the catalyst to the high propylene levels. It is thus advantageous to introduce propane into the gas flow comprising the propylene, which allows partial elimination of the heat of reaction and consequently an increase in the propylene content.

European Patent Application EP 293 224 describes the oxidation in 2 stages of propylene to acrylic acid and in particular, the oxidation reaction of propylene to acrolein in the presence of 5 to 70% by volume of a saturated aliphatic hydrocarbon (1 to 5C) such as propane for example and 3 to 50% by volume of carbon dioxide, used as inert gases. The saturated aliphatic hydrocarbons implemented have a specific heat of approximately 300° C. at constant pressure, higher than that of nitrogen or air. Thus, the gas added is capable of partially absorbing the heat produced by the oxidation reaction. Therefore, it is possible to increase the propylene content in the reaction gas and to produce a larger quantity of acrylic acid. Commercially speaking, it is possible to envisage preparation of the starting gases by using the gases recovered after the 1st stage of the reaction. However, it is not specified whether a conversion of the propane introduced is in fact implemented. Moreover, it was not easy to convert propane to propylene on an industrial scale while avoiding the formation of numerous reaction by-products which could adversely affect subsequent operations.

U.S. Pat. No. 6,492,548 describes the conversion of propane to propylene, then to acrolein and to acrylic acid. The presence of propane in the oxidation of propylene to acrolein phase improves the efficiency of this reaction phase. At the end of the acrolein preparation reaction, it is advantageous to recycle the propane into a reactor intended for its oxidation to propylene, preferably producing low rates of propane conversion and high propylene selectivities. The oxidation of propane to propylene is carried out in the presence of a catalyst such as for example a mixed metal oxide comprising molybdenum, vanadium, tellurium and at least one other element chosen from niobium, tungsten, titanium, etc. or antimony as essential elements. The propane oxidation reaction is generally carried out at a temperature comprised between 200 and 550° C. The conversion reaction of propylene to acrolein is carried out in a catalytic medium at a high temperature. Numerous by-products formed during the course of the reaction must be separated. According to the teaching of FIG. 2, at the outlet from the acrylic acid recovery unit, the stream of unreacted gases, comprising propane, propylene, oxygen, carbon monoxide and carbon dioxide (and optionally nitrogen) is routed into a recycling stream, then compressed and reintroduced continuously, into the propane→propylene→acrolein→acrylic acid conversion process. However, it is known that catalysts used for the conversion of propane to propylene (MoVNb oxides) result in the formation of acrylic acid in addition to propylene. Acrylic acid formed at this stage is routed to the reactor for propylene to acrolein conversion, where it can have a negative effect on the reaction.

It is known that the catalytic oxidation of propane can result in a high number of reaction products, depending on the operating conditions used. L. Luo, J. A. Labinger and M. E. Davis, J. of Catalysis, 200, 222-231 (2001) have described the different routes for the of partial catalytic oxidation of propane in the presence of metal oxides, which can be summarised by the diagram shown in FIG. 1, comprising 3 major reaction routes:

The specific orientation towards one or other of the oxidation products, with industrial performance yields, requires the parameters for implementation of said oxidation to be set very accurately. It is easily understood that numerous reaction by-products can form, which can prove to be a handicap in the behaviour of the reaction or in the isolation of the desired product.

It has been shown that the presence of acrylic acid can significantly interfere with the stage of propylene to acrolein conversion. Thus, in the industrial preparation of acrylic acid, unreacted gas recycling operations can prove to be no longer a real advantage but a significant drawback, due to the quantities of acrylic acid which are poorly separated from the gas flow, and which are present during the propylene to acrolein conversion.

SUMMARY OF THE INVENTION

The invention relates to a method for preparing acrylic acid by oxidizing propylene and then acrolein, involving the recycling of gases that had not reacted by means of a partial oxidation of the propane, in parallel, at the end of the acrylic acid recovery step, then returning, to the propylene-converting reactor, a gas rich in both propane and propylene having been subjected to a second passage in the acrylic acid recovery column.

DETAILED DESCRIPTION OF THE INVENTION

Figure 1:
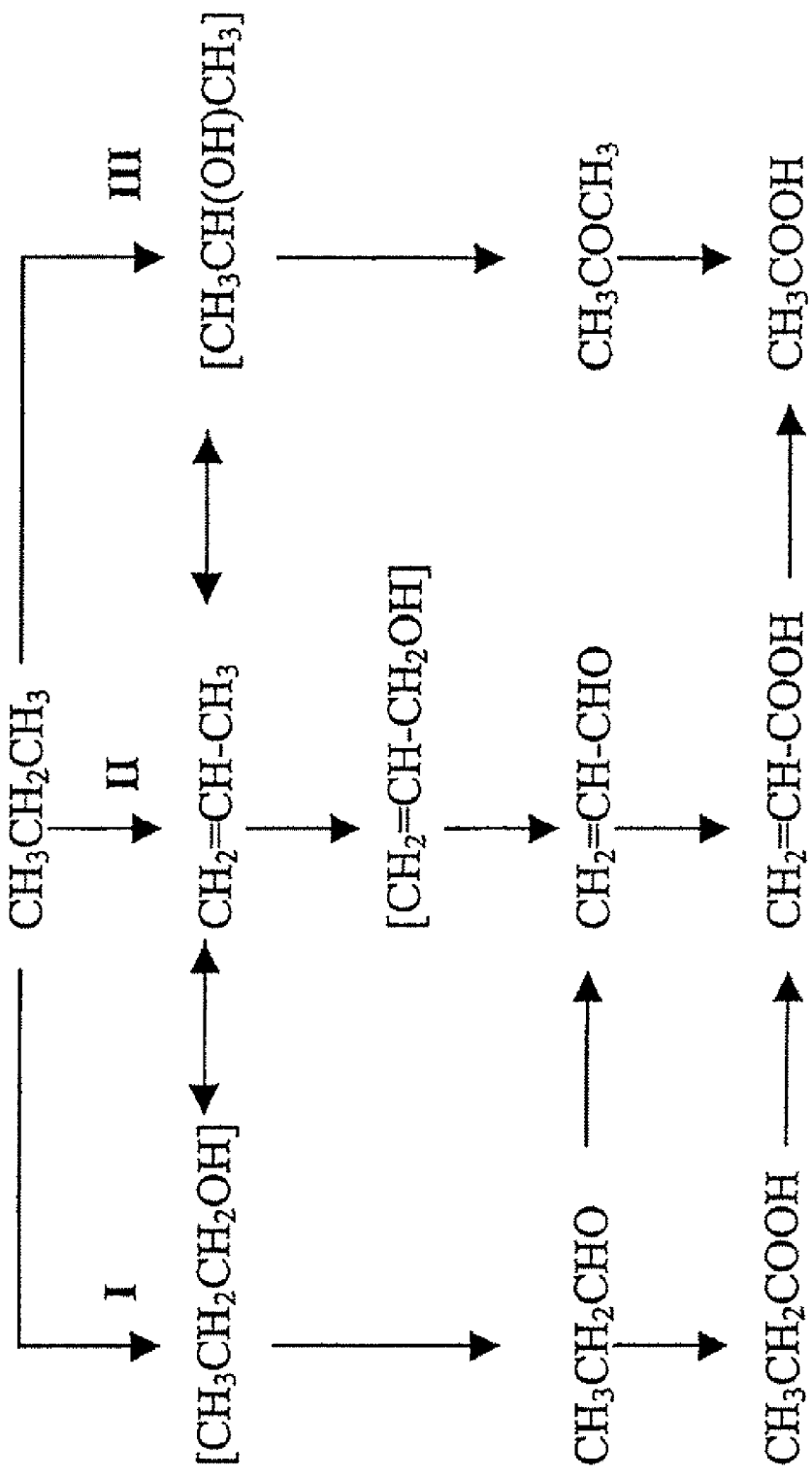
FIG. 1 is a flowchart depicting the different routes for the of partial catalytic oxidation of propane in the presence of metal oxides.
Figure 2:
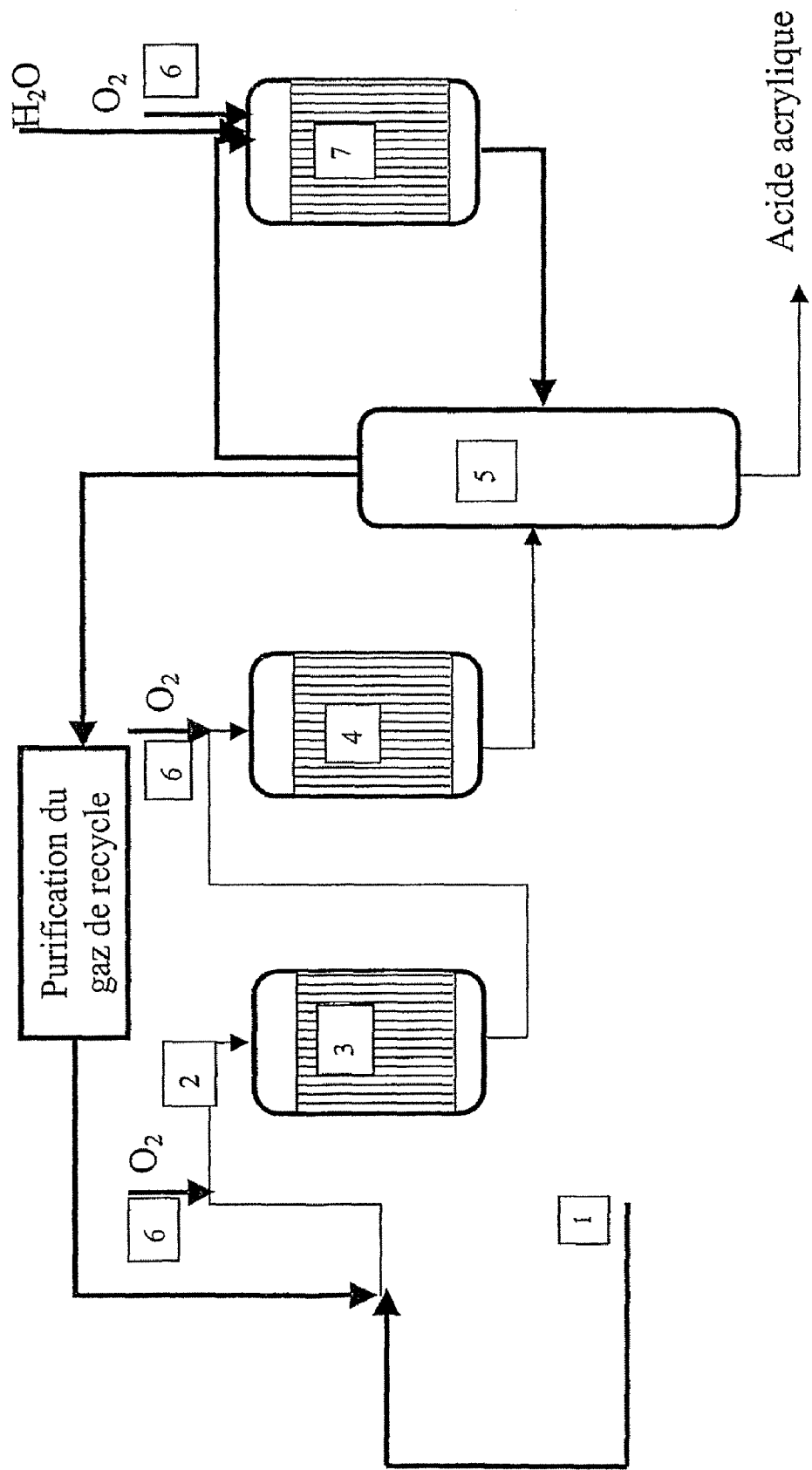
FIG. 2 is a schematic diagram of an installation device allowing implementation of the process for the preparation of acrylic acid, with recycling of the unreacted gases, comprising partial oxidation of the propane in parallel.

It has now been found, and this is the subject of the present invention, that preparation of acrylic acid by oxidation of propylene then acrolein can be implemented with recycling of the unreacted gases, more particularly with partial oxidation of propane, by carrying out this oxidation in parallel at the outlet of the acrylic acid recovery stage, then by returning to the propylene conversion reactor a gas rich in propane and propylene which has undergone a second pass through the acrylic acid recovery column, as shown in FIG. 2.

This improvement in the preparation process for acrylic acid from propylene consists of a partial conversion to propylene of propane used as inert gas in the first stage of oxidation of propylene to acrolein and recovery at the outlet from the second stage of conversion to acrylic acid, in such a way as to allow the starting level of propylene to be increased while maintaining partial pressures of propane at a sufficiently high level. A significant advantage of this process is to remove acrylic acid from the gas flow and to avoid the introduction of this acid into the propylene-to-acrolein oxidation reactor. Another advantage is to increase the acrylic acid yield (majority by-product of the partial oxidation reaction of propane) and also to limit the formation of secondary by-products such as propionic acid or acetone.

According to the invention, the propane undergoes partial conversion to propylene in a reactor placed in parallel with the adsorption column intended for acrylic acid recovery. This partial conversion takes place in the presence of a catalyst constituted by a mixture of oxides and under specific operating conditions allowing the formation of by-products such as, in particular, propionic acid and acetone to be limited, and propylene to be obtained as the majority product. The gas flow is then reintroduced into the adsorption column used for the recovery of acrylic acid, then routed to the reactor for propylene to acrolein conversion.

According to the invention, the process of partial oxidation of propane to propylene is implemented at a high temperature (300 to 500° C. and preferably greater than 380° C., up to 450° C.) and at high volume velocities per hour VVH (flow of reaction gas/volume of catalyst). Advantageously, the operation takes place at a VVH greater than 10000 h$^{-1}$ and preferably comprised between values greater than 10,000 h$^{-1}$, and 20,000 h$^{-1}$.

According to the invention, the catalyst used for the partial oxidation of propane to propylene is a mixture of oxides containing elements chosen from molybdenum, vanadium, tellurium or antimony, niobium or tantalum, the silicon corresponding to the structure:

$$Mo_1V_a(Te \text{ or } Sb)_b(Nb \text{ or } Ta)_cSi_dO_x \qquad (I)$$

in which:
a is comprised between 0.006 and 1, inclusive;
b is comprised between 0.006 and 1, inclusive;
c is comprised between 0.006 and 1, inclusive;
d is comprised between 0 and 3.5, inclusive; and
x is the quantity of oxygen bound to the other elements and depends on their oxidation states.

The catalyst of formula (Ia)

$$Mo_1V_aSb_bNb_cSi_dO_x \qquad (Ia)$$

in which a, b, c, d and x are defined as above, is quite particularly preferred.

More particularly preferred are also catalysts (I) or (Ia) in which:
a is comprised between 0.01 and 0.06, inclusive;
b is comprised between 0.01 and 0.5, inclusive;
c is comprised between 0.006 and 0.3, inclusive;
d is comprised between 0 and 2, inclusive; and
x is the quantity of oxygen bound to the other elements and depends on their oxidation states.

The catalyst can be formed on an inert support, according to the techniques known to a person skilled in the art and applied to fixed-bed reactors. For example, it can be formed by extrusion, pelleting, coating, impregnation and preferably by coating.

The oxides of the different metals included in the composition of the catalyst of formula (I) can be used as raw materials in the preparation of this catalyst, but the raw materials are not limited to oxides; among the raw materials which can be used, the following, which are not limitative, can be mentioned:

in the case of molybdenum, ammonium molybdate, ammonium paramolybdate, ammonium heptamolybdate, molybdic acid, molybdenum halides or oxyhalogenates such as $MoCl_5$, organometallic compounds of molybdenum such as molybdenum alkoxides such as $Mo(OC_2H_5)_5$, acetylacetone molybdenyl;

in the case of vanadium, ammonium metavanadate, vanadium halides or oxyhalogenates such as $VCl_4$, $VCl_5$ or $VOCl_3$, organometallic compounds of vanadium such as vanadium alkoxides such as $VO(OC_2H_5)_3$;

in the case of antimony, for example antimony oxide (antimony trioxide), in particular the senarmontite variety, antimony sulphate $(Sb_2(SO_4)_3)$ or an antimony chloride (antimony trichloride, antimony pentachloride);

in the case of tellurium, tellurium, telluric acid, $TeO_2$;

in the case of the niobium, niobic acid, niobium tartrate, niobium hydrogen oxalate, oxotrioxalateammonium niobiate $\{(NH_4)_3[NbO(C_2O_4)_3]*1.5H_2O\}$, niobium and ammonium oxalate, niobium oxalate and tartrate, niobium halides or oxyhalogenates such as $NbCl_3$, $NbCl_5$ and organometallic compounds of niobium such as niobium alkoxides such as $Nb(OC_2H_5)_5$, $Nb(O-n-Bu)_5$;

in the case of tantalum, tantalum oxalate;

and generally, all compounds capable of forming an oxide by calcination, namely, metallic salts of organic acids, metallic salts of inorganic acids, metal complex compounds, etc.

The source of silicon is generally constituted by colloidal silica and/or polysilicic acid.

By way of example, the catalyst support is advantageously silica, alumina, aluminosilicate, steatite, a ceramic or silicon carbide.

A method for the preparation of the catalysts comprises mixing under stirring aqueous solutions of niobic acid or tantalum oxalate, oxalic acid, ammonium heptamolybdate, ammonium metavanadate, telluric acid or antimony oxide, if appropriate adding colloidal silica, then preferably precalcinating under air at approximately 300-320° C., and calcinating under nitrogen at approximately 600° C.

According to a preferred embodiment, a process for the preparation of the catalysts consists of the preparation of a solution of niobic acid and oxalic acid, or the use of a solution of commercial tantalum oxalate, then preparation of a solution of molybdenum, vanadium, tellurium or antimony, followed by mixing the 2 solutions, resulting in the formation of a gel, drying the gel obtained, and precalcination then calcination.

According to a particularly preferred process, the catalyst can be prepared by implementing the following stages:

1) dissolution in water of a source of vanadium, for example, ammonium metavanadate, under stirring and optionally, while heating;
2) if appropriate, addition to the solution obtained previously of a source of tellurium or antimony, for example telluric acid, or antimony oxide (in particular the senarmontite variety);

3) addition of a source of molybdenum, for example, ammonium heptamolybdate;
4) reaction of the solution obtained, under reflux;
5) if appropriate, addition of a oxidizing agent such as hydrogen peroxide in the case of antimony catalysts;
6) if appropriate, addition of a solution prepared by mixing, under heating, a source of niobium, for example, niobic acid, with oxalic acid;
7) reaction of the reaction mixture under reflux and preferably under an inert atmosphere, until a gel is obtained;
8) drying the gel obtained;
9) preferably precalcination of the gel; and
10) calcination of the gel, optionally precalcinated, in order to obtain the catalyst.

The source of silicon (colloidal silica and/or polysilicic acid) is advantageously added after stage 5). It is also possible to add it after the drying or precalcination stages.

In alternatives to the above processes:
drying [for example in stage 8)] can be carried out in a thin layer in an oven, by atomization, lyophilization, zeodration, by microwaves, etc;
precalcination can be carried out under an air flow at 280~300° C. or under static air at 320° C., in a fluidized bed, in a rotary oven in a fixed bed called aerated, in such a way that the particles of catalyst are separated from one another to prevent them from fusing together during precalcination or possibly during calcination;
calcination is preferably carried out under very pure nitrogen and at a temperature close to 600° C., for example in a rotary oven or in a fluidized bed and for a duration which can be 2 hours.

According to the preferred embodiments of the precalcination, the operation is carried:
either at a temperature below 300° C. under an air flow of at least 10 ml/min/g of catalyst; in particular at approximately 290° C., under an air flow of approximately 50 ml/min/g.
or at a temperature ranging from 300 to 350° C. under an air flow of less than 10 ml/min/g of catalyst; in particular at approximately 320° C. under an air flow of less than 10 ml/min/g.

According to another method for the preparation of catalysts, a solid-solid reaction is carried out by mixing the metal sources then co-grinding until a uniform mixture is obtained. The solid is obtained after heating under reduced pressure at a temperature close to 600° C.

Advantageously, metal oxides or the metal itself are used as the metal source. More preferentially, heating is carried out for a prolonged period (preferably 3 days to 1 week).

The catalysts prepared according to the processes described above can each be presented in the form of particles, generally with a diameter of 20 to 300 µm, the particles of each of the combined catalysts generally being mixed before carrying out the process according to the invention. Shaping can be carried out by atomization of a gel or a suspension. For use in a fixed bed, the catalysts can be presented in the form of beads or cylinders or also hollow cylinders with a diameter of 3 to 10 mm, preferably 5 to 8 mm, coated with active ingredient.

Installation Device

FIG. 2 describes an installation device allowing implementation of the process for the preparation of acrylic acid, with recycling of the unreacted gases, comprising partial oxidation of the propane in parallel. It is understood that this installation device also falls within the scope of the present invention.

In FIG. 2, the elements numbered from 1 to 7 have the following meanings:
1: Fresh load of propylene/propane
2: Reaction mixture (propane, propylene, steam, oxygen)
3: Propylene-to-acrolein conversion reactor.
4: Acrolein-to-acrylic acid conversion reactor
5: Absorption column
6: Oxygen addition port
7: Propane conversion reactor.

The invention also relates to a device intended for the preparation of acrylic acid comprising:
a) a first reactor for the oxidation of propylene to acrolein [3], continuously feeding
b) a second reactor intended for the oxidation of acrolein to acrylic acid [4], connected to
c) an absorption column [5] intended for the recovery of acrylic acid, the unreacted gases being routed to
d) a reactor for the partial oxidation of propane to propylene [7], arranged in parallel with the outlet of the absorption column [5], said gases undergoing at the outlet a further pass through the absorption column or a similar column, then
e) recycling into the first propylene oxidation reactor [3].

In FIG. 2, the reactor [7], arranged in parallel with the absorption column [5] allowing recovery of the acrylic acid, is intended for partial oxidation of the propane to propylene. The gas flow leaving column [5] is routed to the reactor [7] containing a bed of catalyst based on the mixture of oxides. This gas flow principally contains propane, unreacted propylene, steam, carbon monoxide, carbon dioxide, residual oxygen and optionally inert gases (argon), acrolein and acetone. A gas flow comprising a mixture of steam/molecular oxygen/optionally inert gas, is also introduced into the reactor [7].

Preferably the catalyst bed is a fixed bed: in particular a co-feed fixed bed. According to another alternative, use of a fluidized bed or a transported bed can also be envisaged.

The propane/oxygen molecular ratio is greater than 1 and preferably greater than, or equal to, 4. In the gaseous mixture implemented in the propane partial oxidation reaction, the propane content must be at least greater than 20% and less than 90%.

The propane/steam ratio by volume in the gaseous mixture introduced overall into the reactor [7] is not critical and can vary within wide limits. It is not essential to introduce steam in great quantities, it is even possible for steam to be absent from the gaseous mixture.

Similarly, the proportion of inert gases, which can be helium, krypton, a mixture of these two gases, argon or nitrogen, carbon dioxide, etc., is not critical either and can also vary within wide limits.

The proportions of the constituents of the initial gaseous mixture are generally the following (in molar ratios):

propane/oxygen/inert gas (Ar, $N_2$, $CO_2$)/$H_2O$ (steam) =1/0.05-2/0-12/0.1-10.

Preferably, they are 1/0.1-1/0-11/0.3-6.

Pressure in the reactor is generally set from $1.01.10^4$ to $1.01.10^6$ Pa (0.1 to 10 atmospheres), preferably $5.05.10^4$ to $5.05.10^5$ Pa (0.5-5 atmospheres). Preferably, for fixed-bed operation, the pressure is set at $2.10^5$ Pa.

At the outlet of the reactor [7], the gas flow rich in propane and propylene is reintroduced into the absorption column [5] (or optionally into a second similar absorption column. In this case the effluents of the second column can feed the first column). In the acrylic acid absorption column/s, the by-product of the oxidation reaction in the reactor [7], is recovered. Thus the gas flow routed by recycling to the reactor for the conversion of propylene to acrolein [3] is cleaned of the residual acrylic acid.

The reactor for the conversion of propylene to acrolein [3] receives a mixture of a fresh propylene/propane load [1] and the recycled reaction mixture (comprising propylene/propane/steam/oxygen/optionally inert gases) [2], as well as an addition of molecular oxygen [6]. Principally, the inert gases can be nitrogen, carbon dioxide, argon as well as other gases carried by the recycled gas, such as methane, ethane, etc.

It is important to select a catalyst which encourages the conversion of propylene to acrolein, but which is not sensitive to the presence of propane. Generally the reaction is catalysed by a catalyst such as a bismuth molybdate, to a temperature close to 320° C. and under a pressure of $2.10^5$ Pa. The catalyst can be chosen for example from the molybdates described in Table 2 of the publication by M. Tanimoto, Shokubai, 45(5), 360 (2003).

The fresh propylene/propane load [1] can be a propylene cut originating from a steam cracker. In this case the propane content is approximately 5%. It is also possible to use a propylene/propane cut from oil refineries.

Advantageously, the propane content in the fresh propylene/propane load should be at least 5%.

The overall proportion of propylene/propane/steam/oxygen/optionally inert gases received by the reactor must be such that high propane partial pressures are ensured. This proportion is situated preferably within the limits 5 to 15/30 to 50/0 to 15/5 to 20/0 to 50.

The gas flow output from the reactor [3] is routed to the reactor for acrolein to acrylic acid conversion [4].

The reactor [4] receives the gaseous mixture originating from the reactor [3] which is then oxidized to acrylic acid in the presence of a catalyst which encourages the conversion of the acrolein to acrylic acid, but which is not sensitive to the presence of propane. Generally the reaction is catalysed by a catalyst such as a mixed oxide based on molybdenum and vanadium under a pressure of $2.10^5$ Pa and at a temperature close to 250° C. The catalyst can be chosen for example from the mixed oxides described in Table 3 of the publication by M. Tanimoto, Shokubai, 45(5), 360 (2003).

The present invention has the great advantage of combining very good acrylic acid selectivity and good propylene conversion, as a result of gas recycling which ensures both high partial pressures of propane in the reactor for the oxidation of propylene to acrolein, a higher proportion of propylene introduced and very low proportions of acrylic acid at the level of this first stage of oxidation. Moreover, passage of the gas flow originating from the propane partial conversion reactor into the absorption column, allowing acrylic acid to be isolated, ensures an addition to the yield of acrylic acid, the latter being the main reaction by-product in the partial conversion of propane to propylene.

It is understood that the present invention also relates to the use of the process described above, for the preparation of acrylic acid.

This advantage can be observed in particular in the following tests.

EXAMPLES

The following examples illustrate the present invention without however limiting its scope.

Preparation of Catalysts for the Partial Oxidation of Propane to Propylene

Example A

Preparation of Catalyst A:
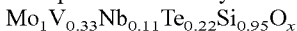

Preparation of a Solution of Niobium:
The following are placed in a 5-litre beaker:
640 g of distilled water,
then 51.2 g of niobic acid, i.e. $n_{Nb}$=0.304 moles;
and finally 103.2 g of oxalic acid dihydrate, i.e. $n_{oxalate}$=0.816 moles.
The oxalic acid/Nb molar ratio is 2.69 in this case.
The mixture is heated at 60° C. (a beaker cover is placed on the beaker to prevent evaporation) for 2 hours under stirring. A white suspension is obtained. The mixture is allowed to cool to 30° C. under stirring (cooling for approximately 2 hours).

In parallel, a solution of Mo, V, Te is prepared in the following manner:
The following are placed in a 5-litre beaker:
2120 g of distilled water,
then 488.0 g of ammonium heptamolybdate, i.e. $n_{Mo}$=2.768 moles;
then 106.4 g of ammonium metavanadate, i.e. $n_v$=0.912 moles;
and finally 139.2 g of telluric acid, i.e. $n_{Te}$=0.608 moles.
The mixture is heated at 60° C. (a beaker cover is placed on the beaker to prevent evaporation) for 1 hour 20 min and a clear red solution is obtained. The mixture is allowed to cool to 30° C. while stirring (cooling for 2 hours).

Introduction of the Silica:
393.6 g of Ludox silica (40% by weight of silica AS40) is introduced, under stirring, into the solution of Mo, V, Te prepared as above. The solution remains clear and red, but a little more diluted. The niobium solution is introduced into that of (Mo, V, Te, Si) and a fluorescent orange gel is obtained after stirring for a few minutes. This solution is then dried by atomization (laboratory atomizer—ATSELAB from Sodeva). The atomization takes place under a nitrogen atmosphere.

The working parameters are overall:
nitrogen flow rate approximately 45 Nm³/h;
slurry flow rate of approximately 500 g/h;
inlet temperature of the gas comprised between 155° C. and 170° C.;
outlet temperature of the gas comprised between 92° C. and 100° C.

The product of particle size less than 40 microns (355.2 g), recovered in the cyclone, is put in an oven overnight at 130° C. in a Teflon®-covered plate. 331 g of dry product is recovered.

Pre-calcination and Calcination:
The 331 g of precursor is precalcinated for 4 hours at 300° C. under an air flow (47.9 ml/min/g), producing a solid which is calcinated for 2 hours at 600° C. under a nitrogen flow (12.8 ml/min/g). The catalyst A is thus obtained.

The calcinations are carried out under air and nitrogen flow in steel capacitors. These capacitors are directly installed in muffle furnaces and the air is supplied via the chimney. An internal thermometer well allows precise monitoring of the temperature. The cover is useful in the case of calcinations under nitrogen to prevent air returning towards the catalyst.

Example B

Preparation of a Catalyst B of Formula: $Mo_1V_{0.30}Sb_{0.15}Nb_{0.10}Si_1O_x$ and Its Precursor Symbolised by the Formula

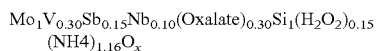

Synthesis of the Precursor:

Approximately 100 g of dry precursor is prepared in this way.

Stage 1: Dissolution-Precipitation

Solution A 12.3 g (0.1052 mole V) of ammonium metavanadate (AMV) (producer GfE), 7.7 g (0.0528 mol Sb) of $Sb_2O_3$ (Producer CAMPINE), 61.8 g of ammonium heptamolybdate (AHM, 0.3501 mole of Mo) (Producer Starck) are placed in solution in 130 ml of demineralised water, under stirring, in a 1-litre SVL® glass reactor, heated in a thermostatically-controlled oil bath at 128° C. A gentle 20 ml addition of water is necessary to rinse the funnel. After the addition of AHM, the reactor is placed under nitrogen flushing, the reaction is maintained under stirring, under reflux, for 4 hours. A yellow suspension is obtained which progressively changes to blue-black.

Solution B 6 g (0.0530 mol) of an aqueous solution of $H_2O_2$ at 30% by weight, dissolved in 50 g of water, is then added slowly (1 to 2 minutes approximately). In order to obtain a clear orange solution, 8 drops of pure hydrogen peroxide are added.

Solution C 52.6 g of Ludox® silica AS40 ($n_{si}$=0.350 mole) are added in one go. The solution becomes slightly cloudy. The solution formed is called solution C.

Solution D

A solution D is prepared at the same time as solution A. 100 g of distilled water, 5.9 g of niobic acid marketed by the Brazilian company CBMM are introduced into a 500 ml beaker, i.e. $n_{Nb}$=0.035 mole, and 13.2 g of Prolabo oxalic acid, i.e. $n_{oxalates}$=0.105 mole. The mixture is heated at 70° C. under stirring for 2 hours, then cooled down to 30° C. The solution is then centrifuged at 6200 rpm for 12 minutes in order to obtain a clear solution.

Solution D is added to solution C, in one go. A fluid orange, then yellow, gel is obtained. Stirring is maintained for 30 minutes under a flow of nitrogen, under reflux.

Stage 2: Drying

The gel is then dried in a ventilated oven, on Teflon®-covered plates overnight, at 130° C. 111.4 g of dry precursor is recovered. The precursor is presented in the form of leaves, black on top with a thin green film underneath. Thus a precursor is obtained, symbolised by the following formula, showing the main constituents:

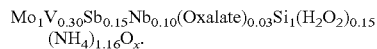

Stage 3: Heat Treatment 30 g of precursor obtained previously is precalcinated to 317° C. under static air.

After calcination at 594° C. under a nitrogen flow of 49.8 ml/min/g, a solid calcinated mass of 24.4 g is obtained. This catalyst is called CATALYST B.

Partial Oxidation of Propane

In the following examples, the yields, selectivities and conversion of propane are defined as follows:

Acrylic acid yield (TTU) (%)=number of moles of acrylic acid formed/number of moles of propane introduced×100.

(The yields take account of the number of moles of carbon in each of the products and correspond in fact to the equivalent number of moles of propane having reacted).

Propane conversion = $TTG$(propane)
= sum of the yield in each of the products.

Propane conversion(%) =

$$\frac{\text{Number of moles of propane having reacted}}{\text{Number of moles of propane introduced}} \times 100$$

Acrylic acid selectivity(%) =

$$\frac{\text{Number of moles of acrylic acid formed}}{\text{Number of moles of propane having reacted}} \times 100$$

The selectivities relating to the other compounds are calculated in a similar way.

The analyses are validated when the carbon balance (sum of the yields in all the products detected by analysis including propane) are comprised between 95 and 105%, and when the number of moles of acid measured by sodium carbonate titrimetry corresponds to the number of moles of acid determined by chromatography, to the nearest 10%.

Loading the Reactors

All the laboratory reactors were load according to a similar protocol, an example of which is shown in detail here. The catalyst was diluted with 10 ml silicon carbide 0.125 mm.

Figure 3:
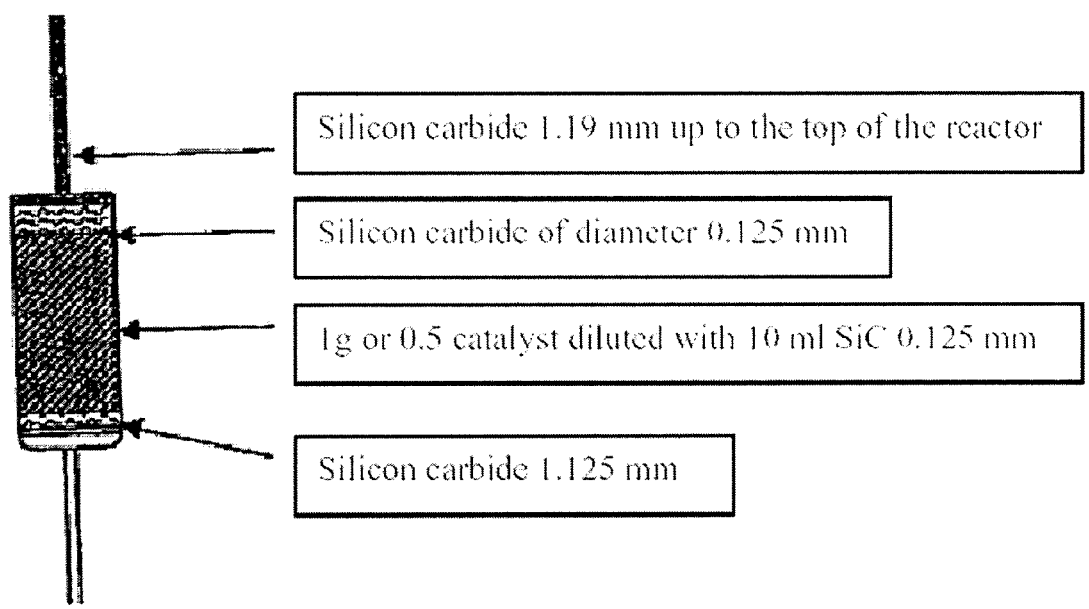
FIG. 3 is a diagram depicting an example of loading the reactor of the present invention.

Example of loading the reactor [7] (in the case of Tests 3 and 4) is shown in FIG. 3.

Apparatus (Example of Loading the Reactor According to Test 1)

The tests are carried out in a fixed-bed reactor.

A cylindrical-shaped vertical reactor made of Pyrex is loaded from bottom to top and comprises:

a first height of 2 ml silicon carbide in the form of particles of 0.125 mm diameter, a second height of 2 ml silicon carbide in the form of particles of 0.062 mm diameter, a third height of 1.00 g of catalyst in the form of particles of 0.02 to 1 mm diluted with 10 ml of silicon carbide in the form of particles of 0.125 mm diameter, a fourth height of 2 ml of silicon carbide in the form of particles of 0.062 mm diameter, a fifth height of 2 ml silicon carbide in the form of particles of 0.125 mm diameter, and a sixth height of silicon carbide in the form of particles of 1.19 mm diameter, so as to fill the whole of the reactor.

TABLE 1

Volume and mass of SiC and Catalyst by order of loading into the reactor

| Load | Balances No. | SiC 0.125 mm | SiC 0.062 mm | Catalyst | SiC 0.125 mm/ dilution | SiC 0.062 mm | SiC 0.125 mm |
|---|---|---|---|---|---|---|---|
| Test 1 | 1 to 4 | 2 ml | 2 ml | Catalyst A 1.005 g (v = 0.9 ml) | 10 ml | 2 ml | 2 ml |
| Test 2 | 1 to 5 | 2 ml | 2 ml | Catalyst A 0.516 g (v = 0.5 ml) | 10 ml | 2 ml | 2 ml |
| Test 3 | 1 to 4 | 4 ml | — | Catalyst B 1.026 g (v = 1 ml) | 10 ml | — | 4 ml |
| Test 4 | 1 to 5 | 4 ml | — | Catalyst B 0.563 g (v = 0.5 ml) | 10 ml | — | 4 ml |

Description of Tests

In order to study the performance of catalysts A and B, we have used co-feed tests. The principal characteristics of these tests and the information collected are as follows:

Co-feed Balance, Under Standard Conditions: Basic Test for Fast Comparison of the Catalysts in Co-feed Mode; Test Conditions (Flow Rates of the Different Gases):

Propane/Oxygen/Helium-Krypton/Water=0.829/0.877/4.267/4.234 (in NL/h). The test temperature is 380° C., 400 and 420° C. With this type of test, the contact time of the gas on the catalyst is approximately 0.35 s according to the density of the catalyst.

Co-feed Balance, with a Double Flow of Helium: Test Conditions:

Propane/Oxygen/Helium-Krypton/Water=0.829/0.877/8.44/4.234 (in NL/h). The test temperatures are 380° C. for 0.5 g catalyst and 420° C. for 1 g catalyst. With a test of this type, the contact times of the gas on the catalyst are approximately 0.13 s for 0.5 g catalyst and of approximately 0.25 s for 1 g.

Co-feed Balance, with a No Helium Flow and Six Times More Propane: Test Conditions:

Propane/Oxygen/Helium-Krypton/Water=5.108/0.877/0/4.234 (in 25 NL/h). The test temperatures are 420 and 440° C. for 0.5 g catalyst. With a test of this type, the contact time of the gas on the catalyst is approximately 0.18 s for 0.5 g of catalyst.

Tests of the Catalysts

1) Procedure

The reactor containing the catalyst is placed in a vertical isotherm oven allowing the reaction temperature to be imposed. The top of the reactor is connected to the common feed of gas and steam.

Heating under a flow of inert gas He/Kr with:
the reactor at 250° C.,
the vaporizer at 200° C.,
electrical actuation of the water pump.

When the vaporizer and the reactor are at the correct temperature, the water pump is actuated. When the temperature is reached and water is present at the outlet of the reactor, the propane and the oxygen are added at their nominal values. The temperature of the reactor is adjusted to the desired temperature, according to the catalyst. The temperature of the reactor and the temperature of the hot spot are allowed to stabilize for a minimum of 30 min.

The balance is carried out by connecting a gas-washing bottle, stored in ice in order to trap condensable products, to the outlet of the reactor, and connected to the μ-GC for in-line analysis of the noncondensable effluents. The condensable effluents recovered are analysed on an HP 6890 chromatograph, as well as by sodium carbonate titration of the number of moles of acid formed.

Results of the Tests

Additional Calculations and Definitions:

The VVH is the volume velocity per hour, and is expressed in $h^{-1}$. It represents the ratio between the gas flow rate at entry and the volume of catalyst. The latter is measured in a test piece. The gas flow at entry is expressed in normal litres (litres of gas measured at 0° C. and 1 atm) per hour.

The contact time is calculated by taking the inverse of the VVH. For reasons of practicality, it is expressed in seconds.

It is possible to obtain a high VVH by increasing the gas flow in the reactor. However, in this case, the resulting pressure drop over the catalyst bed increases. Nevertheless, the productivity of the reactor is also increased thereby.

In general, it is preferred to reduce the mass of catalyst, which does not disturb the hydrodynamics of the reactor and does not result in an increased pressure drop.

The productivity of a product P is calculated as being the number of moles of this product per kg of catalyst and per second. In the present case, we have calculated the productivity in equivalent C3, i.e. the number of micromoles of propane which have reacted in order to produce the number of micromoles of product P, per kg of catalyst and per second. In the case of products with 3 carbons, both productivities are identical. The result is obtained directly by multiplying the yield of product P by the propane entry flow rate and dividing the whole by the mass of catalyst.

Test 1 with 1 g of Catalyst A 4 balances have been carried out under the following conditions Balances 1 to 3:

The gas feed flow rates are propane/oxygen/Helium-Krypton/steam: 0.829/0.877/4.267/4.234 in NL/h. The temperature of the reactor is 380° C., 400 and 420° C.

Balance 4: for this balance the flow rate of Helium-Krypton was doubled—Propane/Oxygen/Helium-Krypton/Water=0.829/0.877/8.44/4.234 (in NL/h)—, and the temperature of the reactor was maintained at 420° C.

TABLE 2

Yields and Selectivities of Test 1

| | TEST 1 | | | |
|---|---|---|---|---|
| | Balance 1 | Balance 2 | Balance 3 | Balance 4 |
| Reaction Temp (° C.) | 380 | 400 | 420 | 420 |
| Hot spot Temp (° C.) | 384.8 | 405 | 425 | 425 |
| Stabilization period: | 00:53 | 01:22 | 00:45 | 00:35 |
| Contact time (s) | 0.32 | 0.32 | 0.32 | 0.23 |
| Gas conditions (Propane/$O_2$/He—Kr/$H_2O$) | 10/10/45/45 | 10/10/45/45 | 10/10/45/45 | 10/10/90/45 |
| Yields | TTUc (%) | | | |
| Acetaldehyde | 0.00 | 0.00 | 0.01 | 0.00 |
| Propanaldehyde | 0.00 | 0.00 | 0.00 | 0.00 |
| Acetone | 0.06 | 0.06 | 0.04 | 0.03 |

TABLE 2-continued

Yields and Selectivities of Test 1

|  |  |  |  |  |
|---|---|---|---|---|
| Acrolein | 0.00 | 0.01 | 0.01 | 0.01 |
| Allyl alcohol | 0.00 | 0.00 | 0.00 | 0.00 |
| Allyl acrylate | 0.00 | 0.00 | 0.00 | 0.00 |
| Acetic acid | 0.12 | 0.21 | 0.31 | 0.18 |
| Propionic acid | 0.03 | 0.03 | 0.02 | 0.01 |
| Acrylic acid | 1.37 | 2.32 | 3.69 | 2.54 |
| CO | 0.08 | 0.22 | 0.52 | 0.29 |
| $CO_2$ | 0.15 | 0.23 | 0.45 | 0.35 |
| Propylene | 2.36 | 3.02 | 3.71 | 3.24 |
| Propane | 96.5 | 94.8 | 94.8 | 93.1 |
| Carbon balance (%) | 100.7 | 100.8 | 103.5 | 99.7 |
| TTG = Sum of TTUs | 4.2 | 6.1 | 8.8 | 6.7 |

| Selectivities (%) | Selectivity (%) | | | |
|---|---|---|---|---|
| Acetaldehyde | 0.08 | 0.07 | 0.06 | 0.06 |
| Propanaldehyde | 0.00 | 0.00 | 0.00 | 0.00 |
| Acetone | 1.51 | 0.92 | 0.49 | 0.47 |
| Acrolein | 0.10 | 0.14 | 0.16 | 0.18 |
| Allyl alcohol | 0.05 | 0.04 | 0.03 | 0.03 |
| Allyl acrylate | 0.00 | 0.00 | 0.00 | 0.00 |
| Acetic acid | 2.99 | 3.43 | 3.49 | 2.76 |
| Propionic acid | 0.62 | 0.43 | 0.24 | 0.20 |
| Acrylic acid | 32.68 | 38.09 | 42.14 | 38.06 |
| CO | 1.85 | 3.56 | 5.90 | 4.38 |
| $CO_2$ | 3.63 | 3.72 | 5.13 | 5.24 |
| Propylene | 56.5 | 49.6 | 42.4 | 48.6 |

TABLE 3

Productivities of Test 1

| Productivities | Balance 1 µmoleC3/ kg · s | Balance 2 µmoleC3/ kg · s | Balance 3 µmoleC3/ kg · s | Balance 4 µmoleC3/ kg · s |
|---|---|---|---|---|
| Acetaldehyde | 0.4 | 0.4 | 0.5 | 0.4 |
| Propanaldehyde | 0.0 | 0.0 | 0.0 | 0.0 |
| Acetone | 6.4 | 5.7 | 4.4 | 3.2 |
| Acrolein | 0.4 | 0.9 | 1.5 | 1.2 |
| Allyl alcohol | 0.2 | 0.2 | 0.3 | 0.2 |
| Allyl acrylate | 0.0 | 0.0 | 0.0 | 0.0 |
| Acetic acid | 12.8 | 21.3 | 31.3 | 18.8 |
| Propionic acid | 2.7 | 2.6 | 2.2 | 1.3 |
| Acrylic acid | 139.7 | 236.9 | 377.4 | 259.4 |
| CO | 7.9 | 22.2 | 52.8 | 29.8 |
| $CO_2$ | 15.5 | 23.1 | 45.9 | 35.7 |
| Propylene | 241.5 | 308.6 | 379.4 | 331.4 |

Test 2 with 0.5 g of Catalyst A 5 balances were carried out under the following conditions Balances 1 and 3:

The gas feed flow rates are propane/oxygen/Helium-Krypton/steam: 0.829/0.877/4.267/4.234 in NL/h. The temperature of the reactor is 380° C. and 420° C.

Balance 2: for this balance the flow rate of Helium-Krypton was doubled—Propane/Oxygen/Helium-Krypton/Water=0.829/0.877/8.44/4.234 (in NL/h)—, and the temperature of the reactor was maintained at 380° C.

Balances 4 and 5: for these balances, the flow rate of Helium-Krypton was reduced to 0, and the flow rate of propane was significantly increased, giving the following conditions: propane/oxygen/Helium-Krypton/steam: 5.108/0.877/0/4.234 (in NL/h). The temperature of the reactor is 420 and 440° C. Given the high propane flow rates, the productivities of different products were found to be greatly improved thereby.

TABLE 4

Yields and Selectivities of Test 2

| | TEST 2 | | | | |
|---|---|---|---|---|---|
| | Balance 1 | Balance 2 | Balance 3 | Balance 4 | Balance 5 |
| Reaction Temp (° C.) | 380 | 380 | 420 | 420 | 440 |
| Hot spot Temp (° C.) | 384.1 | 383.8 | 424.8 | 429.3 | 454 |
| Stabilization period: | 00:53 | 00:36 | 01:00 | 01:00 | 00:24 |
| Contact time (s) | 0.18 | 0.13 | 0.18 | 0.18 | 0.18 |
| Gas conditions (Propane/$O_2$/He—Kr/$H_2O$) | 10/10/45/45 | 10/10/90/45 | 10/10/45/45 | 60/10/0/45 | 60/10/0/45 |

| Yields | TTUc (%) | | | | |
|---|---|---|---|---|---|
| Acetaldehyde | 0.00 | 0.00 | 0.00 | 0.00 | 0.01 |
| Propanaldehyde | 0.00 | 0.00 | 0.00 | 0.00 | 0.00 |
| Acetone | 0.03 | 0.02 | 0.03 | 0.03 | 0.03 |
| Acrolein | 0.00 | 0.00 | 0.01 | 0.01 | 0.02 |
| Allyl alcohol | 0.00 | 0.00 | 0.00 | 0.00 | 0.00 |
| Allyl acrylate | 0.00 | 0.00 | 0.00 | 0.00 | 0.00 |
| Acetic acid | 0.04 | 0.02 | 0.12 | 0.08 | 0.13 |
| Propionic acid | 0.01 | 0.01 | 0.01 | 0.01 | 0.01 |
| Acrylic acid | 0.53 | 0.32 | 1.48 | 0.94 | 1.58 |
| CO | 0.00 | 0.00 | 0.14 | 0.11 | 0.27 |
| $CO_2$ | 0.13 | 0.13 | 0.21 | 0.10 | 0.23 |
| Propylene | 1.90 | 1.61 | 3.27 | 3.54 | 4.61 |
| Propane | 98.0 | 98.9 | 96.2 | 98.1 | 98.8 |
| Carbon balance (%) | 100.6 | 101.0 | 101.4 | 102.9 | 105.7 |
| TTG = Sum of TTUs | 2.6 | 2.1 | 5.3 | 4.8 | 6.9 |

TABLE 4-continued

Yields and Selectivities of Test 2

| Selectivities (%) | Selectivity (%) | | | | |
|---|---|---|---|---|---|
| Acetaldehyde | 0.10 | 0.08 | 0.09 | 0.06 | 0.08 |
| Propanaldehyde | 0.00 | 0.00 | 0.00 | 0.02 | 0.02 |
| Acetone | 1.15 | 0.82 | 0.55 | 0.56 | 0.38 |
| Acrolein | 0.10 | 0.10 | 0.23 | 0.24 | 0.29 |
| Allyl alcohol | 0.05 | 0.00 | 0.03 | 0.02 | 0.01 |
| Allyl acrylale | 0.00 | 0.00 | 0.00 | 0.00 | 0.00 |
| Acetic acid | 1.43 | 0.94 | 2.20 | 1.64 | 1.94 |
| Propionic acid | 0.42 | 0.32 | 0.28 | 0.22 | 0.12 |
| Acrylic acid | 19.9 | 15.2 | 28.0 | 19.5 | 22.9 |
| CO | 0.00 | 0.00 | 2.65 | 2.37 | 3.95 |
| $CO_2$ | 4.77 | 6.01 | 3.89 | 2.01 | 3.36 |
| Propylene | 72.1 | 76.6 | 62.1 | 73.4 | 66.9 |

TABLE 5

Productivities of Test 2

| Productivities | Balance 1 | Balance 2 | Balance 3 | Balance 4 | Balance 5 |
|---|---|---|---|---|---|
| | μmoleC3/kg · s | | | | |
| Acetaldehyde | 0.5 | 0.3 | 1.0 | 3.6 | 6.5 |
| Propanaldehyde | 0.0 | 0.0 | 0.0 | 1.1 | 1.3 |
| Acetone | 6.1 | 3.4 | 5.8 | 33.1 | 31.8 |
| Acrolein | 0.5 | 0.4 | 2.4 | 14.1 | 24.6 |
| Allyl alcohol | 0.2 | 0.0 | 0.3 | 1.0 | 1.2 |
| Allyl acrylate | 0.0 | 0.0 | 0.0 | 0.0 | 0.0 |
| Acetic acid | 7.5 | 3.9 | 23.1 | 97.0 | 164.3 |
| Propionic acid | 2.2 | 1.3 | 2.9 | 13.2 | 10.5 |
| Acrylic acid | 104.6 | 63.7 | 293.9 | 1155.6 | 1936.2 |
| CO | 0.0 | 0.0 | 27.8 | 140.2 | 334.1 |
| $CO_2$ | 25.0 | 25.2 | 40.9 | 119.2 | 284.2 |
| Propylene | 378.3 | 321.5 | 652.0 | 4343.5 | 5656.3 |

In all the tests, Test 1, balances 1 to 4 and Test 2, balances 1 to 3, it is noted that as the contact time reduces, the propane selectivity (majority product) increases, and that the sum of the acrylic acid+propylene selectivities increases. Catalyst A thus allows operation with a high propylene selectivity and a high overall selectivity of acrylic acid+propylene, at a low conversion.

The results of balances 4 and 5 of Test 2, show that when the partial pressure of propane is approximately 50%, it is possible to have high productivities of propylene and acrylic acid, while working at a low conversion. Also in this case, the selectivities of useful products remain particularly high.

Test 3 with 1 g of Catalyst B—Carried out as in Test 1 but with an Antimony and Not a Tellurium Catalyst.

4 balances were carried out under the following conditions:

Balances 1 to 3:

The gas feed flow rates are propane/oxygen/Helium-Krypton/steam: 0.829/0.877/4.267/4.234 (in NL/h). The temperature of the reactor is 380, 400 and 420° C.

Balance 4: for this balance the flow rate of Helium-Krypton was doubled—Propane/Oxygen/Helium-Krypton/Water=0.829/0.877/8.44/4.234 (in NL/h), and the temperature of the reactor was maintained at 420° C.

TABLE 6

Yields and Selectivities of Test 3

| | TEST 3 | | | |
|---|---|---|---|---|
| | Balance 1 | Balance 2 | Balance 3 | Balance 4 |
| Reaction Temp (° C.) | 380 | 400 | 420 | 420 |
| Hot spot Temp (° C.) | 386 | 406.6 | 427 | 426 |
| Stabilization period: | 00:55 | 01:00 | 00:45 | 00:35 |
| Contact time (s) | 0.35 | 0.35 | 0.35 | 0.25 |
| Gas conditions (Propane/$O_2$/He—Kr/$H_2O$) | 10/10/ 45/45 | 10/10/ 45/45 | 10/10/ 45/45 | 10/10/ 90/45 |
| Yields | TTUc (%) | | | |
| Acetaldehyde | 0.00 | 0.00 | 0.01 | 0.00 |
| Propanaldehyde | 0.00 | 0.00 | 0.00 | 0.00 |
| Acetone | 0.10 | 0.09 | 0.07 | 0.05 |
| Acrolein | 0.01 | 0.01 | 0.02 | 0.01 |
| Allyl alcohol | 0.00 | 0.00 | 0.00 | 0.00 |
| Allyl acrylate | 0.00 | 0.00 | 0.00 | 0.00 |
| Acetic acid | 0.18 | 0.29 | 0.39 | 0.22 |
| Propionic acid | 0.03 | 0.03 | 0.02 | 0.01 |
| Acrylic acid | 1.67 | 2.56 | 3.60 | 2.40 |
| CO | 0.18 | 0.33 | 0.55 | 0.29 |
| $CO_2$ | 0.19 | 0.28 | 0.43 | 0.27 |
| Propylene | 2.99 | 3.58 | 4.17 | 3.59 |
| Propane | 96.7 | 93.9 | 91.5 | 92.9 |
| Carbon balance (%) | 102.1 | 101.1 | 100.8 | 99.7 |
| TTG = Sum of TTUs | 5.4 | 7.2 | 9.3 | 6.9 |
| Selectivities (%) | Selectivities (%) | | | |
| Acetaldehyde | 0.06 | 0.06 | 0.07 | 0.06 |
| Propanaldehyde | 0.00 | 0.00 | 0.00 | 0.00 |
| Acetone | 1.83 | 1.24 | 0.78 | 0.73 |
| Acrolein | 0.14 | 0.14 | 0.17 | 0.19 |
| Allyl alcohol | 0.00 | 0.00 | 0.00 | 0.00 |
| Allyl acrylate | 0.00 | 0.00 | 0.00 | 0.00 |
| Acetic acid | 3.43 | 4.02 | 4.18 | 3.16 |
| Propionic acid | 0.65 | 0.43 | 0.26 | 0.21 |
| Acrylic acid | 31.2 | 35.7 | 38.9 | 35.1 |
| CO | 3.33 | 4.62 | 5.93 | 4.17 |
| $CO_2$ | 3.51 | 3.95 | 4.65 | 3.97 |
| Propylene | 55.8 | 49.9 | 45.0 | 52.4 |

TABLE 7

Productivities of Test 3

| Productivities | Balance 1 | Balance 2 | Balance 3 | Balance 4 |
|---|---|---|---|---|
| | | μmoleC3/kg · s | | |
| Acetaldehyde | 0.34 | 0.41 | 0.68 | 0.42 |
| Propanaldehyde | 0.00 | 0.00 | 0.00 | 0.00 |
| Acetone | 9.79 | 8.91 | 7.27 | 5.00 |
| Acrolein | 0.73 | 1.00 | 1.56 | 1.33 |
| Allyl alcohol | 0.00 | 0.00 | 0.00 | 0.00 |
| Allyl acrylate | 0.00 | 0.00 | 0.00 | 0.00 |
| Acetic acid | 18.41 | 28.90 | 38.74 | 21.72 |
| Propionic acid | 3.48 | 3.07 | 2.40 | 1.46 |
| Acrylic acid | 167.58 | 256.34 | 361.07 | 240.97 |
| CO | 17.85 | 33.20 | 55.02 | 28.64 |
| $CO_2$ | 18.83 | 28.41 | 43.15 | 27.27 |
| Propylene | 299.31 | 358.74 | 417.46 | 360.19 |

Test 4 with 0.5 g of Catalyst A—Carried out as in Test 2 but with an Antimony Catalyst 5 balances were carried out under the following conditions Balances 1 and 3:

The gas feed flow rates are propane/oxygen/Helium-Krypton/steam: 0.829/0.877/4.267/4.234 (in NL/h). The temperature of the reactor is 380 and 420° C.

Balance 2: for this balance the flow rate of Helium-Krypton was doubled—Propane/Oxygen/Helium-Krypton/Water=0.829/0.877/8.44/4.234 (in NL/h), and the temperature of the reactor was maintained at 380° C.

Balances 4 and 5: for these balances, the flow rate of Helium-Krypton was reduced to 0, and the flow rate of propane was significantly increased, giving the following conditions: propane/oxygen/Helium-Krypton/steam: 5.108/0.877/0/4.234 (in NL/h). The temperature of the reactor is 420 and 440° C. Given the strong propane flow rates, the productivities of different products were found to be greatly improved thereby.

TABLE 8

Yields and Selectivities of Test 4

| | TEST 4 | | | | |
|---|---|---|---|---|---|
| | Balance 1 | Balance 2 | Balance 3 | Balance 4 | Balance 5 |
| Reaction Temp (° C.) | 380 | 380 | 420 | 420 | 440 |
| Hot spot Temp (° C.) | 386 | 385.8 | 426.6 | 428.3 | 449.7 |
| Stabilization period: | 00:53 | 00:36 | 01:00 | 00:32 | 00:24 |
| Contact time (s) | 0.18 | 0.13 | 0.18 | 0.18 | 0.18 |
| Gas conditions Propane/$O_2$/He—Kr/$H_2O$) | 10/10/45/45 | 10/10/90/45 | 10/10/45/45 | 60/10/0/45 | 60/10/0/45 |

| Yields | TTUc (%) | | | | |
|---|---|---|---|---|---|
| Acetaldehyde | 0.01 | 0.00 | 0.01 | 0.00 | 0.01 |
| Propanaldehyde | 0.00 | 0.00 | 0.00 | 0.00 | 0.00 |
| Acetone | 0.03 | 0.02 | 0.05 | 0.03 | 0.03 |
| Acrolein | 0.00 | 0.00 | 0.01 | 0.01 | 0.02 |
| Allyl alcohol | 0.00 | 0.00 | 0.00 | 0.00 | 0.00 |
| Allyl acrylate | 0.00 | 0.00 | 0.00 | 0.00 | 0.00 |
| Acetic acid | 0.04 | 0.03 | 0.17 | 0.07 | 0.10 |
| Propionic acid | 0.01 | 0.00 | 0.01 | 0.01 | 0.01 |
| Acrylic acid | 0.57 | 0.43 | 1.84 | 0.71 | 0.95 |
| CO | 0.00 | 0.00 | 0.29 | 0.10 | 0.17 |
| $CO_2$ | 0.13 | 0.15 | 0.29 | 0.08 | 0.14 |
| Propylene | 2.05 | 1.88 | 3.68 | 3.27 | 3.97 |
| Propane | 98.7 | 97.4 | 94.6 | 98.6 | 98.7 |
| Carbon balance (%) | 101.6 | 99.9 | 101.0 | 102.9 | 104.1 |
| TTG = Sum of TTUs | 2.9 | 2.5 | 6.4 | 4.3 | 5.4 |

| Selectivities (%) | Selectivity (%) | | | | |
|---|---|---|---|---|---|
| Acetaldehyde | 0.21 | 0.12 | 0.16 | 0.09 | 0.11 |
| Propanaldehyde | 0.00 | 0.00 | 0.00 | 0.02 | 0.03 |
| Acetone | 1.04 | 0.70 | 0.71 | 0.73 | 0.50 |
| Acrolein | 0.16 | 0.14 | 0.23 | 0.25 | 0.29 |
| Allyl alcohol | 0.04 | 0.00 | 0.00 | 0.01 | 0.01 |
| Allyl acrylate | 0.00 | 0.00 | 0.00 | 0.00 | 0.00 |
| Acetic acid | 1.45 | 1.08 | 2.65 | 1.69 | 1.90 |
| Propionic acid | 0.38 | 0.20 | 0.23 | 0.27 | 0.16 |
| Acrylic acid | 20.1 | 17.2 | 29.0 | 16.6 | 17.6 |
| CO | 0.00 | 0.00 | 4.57 | 2.29 | 3.19 |
| $CO_2$ | 4.63 | 5.86 | 4.50 | 1.96 | 2.65 |
| Propylene | 72.0 | 74.7 | 58.0 | 76.1 | 73.5 |

TABLE 9

| Productivities | Productivities of Test 4 | | | | |
|---|---|---|---|---|---|
| | Balance 1 | Balance 2 | Balance 3 | Balance 4 | Balance 5 |
| | μmoleC3/kg · s | | | | |
| Acetaldehyde | 1.1 | 0.6 | 1.8 | 4.2 | 6.6 |
| Propanaldehyde | 0.0 | 0.0 | 0.0 | 1.2 | 2.1 |
| Acetone | 5.4 | 3.2 | 8.2 | 35.3 | 30.3 |
| Acrolein | 0.8 | 0.7 | 2.7 | 11.9 | 17.4 |
| Allyl alcohol | 0.2 | 0.0 | 0.0 | 0.5 | 0.5 |
| Allyl acrylate | 0.0 | 0.0 | 0.0 | 0.0 | 0.0 |
| Acetic acid | 7.5 | 4.9 | 30.7 | 81.8 | 115.4 |
| Propionic acid | 2.0 | 0.9 | 2.7 | 12.8 | 9.7 |
| Acrylic acid | 104.9 | 78.9 | 336.4 | 801.6 | 1073.3 |
| CO | 0.0 | 0.0 | 53.0 | 110.8 | 194.2 |
| CO$_2$ | 24.1 | 26.9 | 52.3 | 94.9 | 160.9 |
| Propylene | 374.9 | 342.6 | 672.8 | 3675.9 | 4472.1 |

In all the tests, Test 3, balances 1 to 4 and Test 4, balances 1 to 3, it is noted that as the contact time is reduced, the propylene selectivity (majority product) increases, and that the sum of the acrylic acid+propylene selectivities increases. Catalyst B therefore allows operation with a high propylene selectivity and a strong high selectivity of acrylic acid+propylene, at a low conversion.

The results of balances 4 and 5 of Test 4 show that when the partial pressure of propane is approximately 50%, it is possible to have high productivities of propylene and acrylic acid, while working at a low conversion. Moreover, in this case also the selectivities of useful products remain particularly high.

It is also noted that the selectivities of propionic acid and acetone reduce with the increase in temperature.

The invention claimed is:

1. A process for the preparation of acrylic acid by catalytic oxidation of propylene and subsequently of acrolein, comprising recycling of unreacted gases by carrying out a partial oxidation of propane to propylene, in the presence of a catalyst having the structure:

$$Mo_1V_aSb_bNb_cS_dO_x \qquad (Ia)$$

in which:
 a is 0.006 to 1, inclusive;
 b is 0.006 to 1, inclusive;
 c is 0.006 to 1, inclusive;
 d is 0 to 3.5, inclusive; and
 x is the quantity of oxygen bound to the other elements and depends on their oxidation states, said partial oxidation being conducted in parallel, at an outlet of the acrylic acid recovery stage,
and then, after having undergone a second pass through a column used for acrylic acid recovery, returning a gas rich in propane and propylene, to the propylene oxidation wherein partial oxidation of propane to propylene is implemented at high volume velocities per hour VVH greater than 10,000 h$^{-1}$.

2. A process according to claim 1, wherein propane undergoes partial conversion to propylene, in a reactor arranged in parallel to an adsorption column recovering acrylic acid, then gas flow is reintroduced into the absorption column.

3. A process according to claim 1, wherein partial oxidation of propane to propylene is implemented at a temperature of 300 to 450° C.

4. A process according to claim 1, wherein acrylic acid is recovered.

* * * * *

UNITED STATES PATENT AND TRADEMARK OFFICE
CERTIFICATE OF CORRECTION

PATENT NO. : 7,732,639 B2
APPLICATION NO. : 11/775014
DATED : June 8, 2010
INVENTOR(S) : Dubois et al.

Page 1 of 1

It is certified that error appears in the above-identified patent and that said Letters Patent is hereby corrected as shown below:

Column 20, line 7 reads "$Mo_1V_aSb_bNb_cS_dO_x$    (Ia)" should read
-- $Mo_1V_aSb_bNb_cSi_dO_x$    (Ia) --

Signed and Sealed this

Twenty-first Day of September, 2010

David J. Kappos
*Director of the United States Patent and Trademark Office*